United States Patent
O'Connor et al.

(10) Patent No.: US 6,481,453 B1
(45) Date of Patent: Nov. 19, 2002

(54) MICROFLUIDIC BRANCH METERING SYSTEMS AND METHODS

(75) Inventors: Stephen D. O'Connor, Pasadena, CA (US); Christoph D. Karp, Pasadena, CA (US); Marci Pezzuto, Altadena, CA (US); Eugene Dantsker, Sierra Madre, CA (US)

(73) Assignee: Nanostream, Inc., Pasadena, CA (US)

(*) Notice: Subject to any disclaimer, the term of this patent is extended or adjusted under 35 U.S.C. 154(b) by 0 days.

(21) Appl. No.: 10/185,860

(22) Filed: Jun. 27, 2002

Related U.S. Application Data (63) Continuation-in-part of application No. 09/550,184, filed on Apr. 14, 2000.
(60) Provisional application No. 60/303,520, filed on Jul. 7, 2001.

(51) Int. Cl.[7] ............................. F17D 3/00; F15C 1/00
(52) U.S. Cl. ............... 137/15.04; 137/240; 137/561 A; 137/833
(58) Field of Search .................... 137/833, 240, 137/15.18, 561 A, 15.04, 15.05; 204/601; 422/101, 103

(56) References Cited

U.S. PATENT DOCUMENTS

| | | | | |
|---|---|---|---|---|
| 3,936,262 A | * | 2/1976 | Hehl | 137/561 A |
| 4,676,274 A | * | 6/1987 | Brown | 137/806 |
| 5,730,187 A | * | 3/1998 | Howitz et al. | 137/803 |
| 5,800,690 A | * | 9/1998 | Chow et al. | 204/451 |
| 5,880,071 A | * | 3/1999 | Parce et al. | 204/453 |
| 5,922,591 A | | 7/1999 | Anderson et al. | 435/287.2 |
| 5,976,336 A | | 11/1999 | Dubrow et al. | 204/453 |
| 5,992,453 A | * | 11/1999 | Zimmer | 137/561 A |
| 6,074,725 A | | 6/2000 | Kennedy | 428/188 |
| 6,117,396 A | | 9/2000 | Demers | 422/100 |
| 6,193,471 B1 | | 2/2001 | Paul | 417/53 |
| 6,263,918 B1 | * | 7/2001 | Lewis et al. | 137/597 |
| 6,321,791 B1 | * | 11/2001 | Chow | 137/833 |

FOREIGN PATENT DOCUMENTS

| | | | |
|---|---|---|---|
| WO | WO 99/19717 | 4/1999 | G01N/25/22 |
| WO | WO 99/60397 | 11/1999 | G01N/33/483 |
| WO | WO 01/04909 | 1/2001 | C25B/9/00 |
| WO | WO 01/74490 | 10/2001 | |

OTHER PUBLICATIONS

Handique, K., et al., "Nanoliter Liquid Metering in Microchannels Using Hydrophobic Patterns," Analytical Chemistry, vol. 72, No. 17, pp. 4100–4109 (2000).

* cited by examiner

*Primary Examiner*—A. Michael Chambers
(74) *Attorney, Agent, or Firm*—Vincent K. Gustafson; Michael F. Labbee (57) ABSTRACT

Microfluidic devices and methods for metering discrete plugs of fluid are provided. The microfluidic devices include a trunk channel and a branch channel having an impedance region. A fluid is supplied to the trunk channel and fills the branch channel to the impedance region. The fluid is then flushed from the trunk channel leaving the branch channel filled. Because the branch channel has a volume, a discrete plug of the fluid having a volume substantially equal to that of the branch channel is formed.

50 Claims, 7 Drawing Sheets

MICROFLUIDIC BRANCH METERING SYSTEMS AND METHODS

STATEMENT OF RELATED APPLICATION(S)

This application is a continuation-in-part of U.S. patent application Ser. No. 09/550,184, filed Apr. 14, 2000 and currently pending; and also claims the benefit of U.S. Provisional Patent Application Ser. No. 60/303,520, filed Jul. 7, 2001 and currently pending.

FIELD OF THE INVENTION

The present invention relates to microfluidic devices and the control and metering of fluid within those devices. These devices are useful in various biological and chemical systems, particularly in systems where fluid metering is important, as well as in combination with other liquid-distribution devices.

BACKGROUND OF THE INVENTION

There has been a growing interest in the manufacture and use of microfluidic systems for the acquisition of chemical and biological information. In particular, when conducted in microfluidic volumes, complicated biochemical reactions may be carried out using very small volumes of liquid. Among other benefits, microfluidic systems improve the response time of reactions, minimize sample volume, and lower reagent consumption. When volatile or hazardous materials are used or generated, performing reactions in microfluidic volumes also enhances safety and reduces disposal quantities.

Traditionally, microfluidic devices have been constructed in a planar fashion using techniques that are borrowed from the silicon fabrication industry. Representative systems are described, for example, in some early work by Manz et al. (Trends in Anal. Chem. (1990) 10(5): 144–149; Advances in Chromatography (1993) 33: 1–66). In these publications, microfluidic devices are constructed by using photolithography to define channels on silicon or glass substrates and etching techniques to remove material from the substrate to form the channels. A cover plate is bonded to the top of the device to provide closure. Miniature pumps and valves can also be constructed to be integral (e.g., within) such devices. Alternatively, separate or off-line pumping mechanisms are contemplated.

More recently, a number of methods have been developed that allow microfluidic devices to be constructed from plastic, silicone or other polymeric materials. In one such method, a negative mold is first constructed, and plastic or silicone is then poured into or over the mold. The mold can be constructed using a silicon wafer (see, e.g., Duffy et al., Analytical Chemistry (1998) 70: 4974–4984; McCormick et. al., Analytical Chemistry (1997) 69: 2626–2630), or by building a traditional injection molding cavity for plastic devices. Some molding facilities have developed techniques to construct extremely small molds. Components constructed using a LIGA technique have been developed at the Karolsruhe Nuclear Research center in Germany (see, e.g., Schomburg et al., Journal of Micromechanical Microengineering (1994) 4:186–191), and commercialized by Micro-Parts (Dortmund, Germany). Jenoptik (Jena, Germany) also uses LIGA and a hot-embossing technique. Imprinting methods in PMMA have also been demonstrated (see, Martynova et.al., Analytical Chemistry (1997) 69: 4783–4789) However, these techniques do not lend themselves to rapid prototyping and manufacturing flexibility. Additionally, the foregoing references teach only the preparation of planar microfluidic structures. Moreover, the tool-up costs for both of these techniques are quite high and can be cost-prohibitive.

A more recent method for constructing microfluidic devices uses a KrF laser to perform bulk laser ablation in fluorocarbons that have been compounded with carbon black to cause the fluorocarbon to be absorptive of the KrF laser (see, e.g., McNeely et aL, "Hydrophobic Microfluidics," SPIE Microfluidic Devices & Systems IV, Vol. 3877 (1999)). This method is reported to reduce prototyping time; however, the addition of carbon black renders the material optically impure and presents potential chemical compatibility issues. Additionally, the reference is directed only to planar structures.

Various conventional tools and combinations of tools are used when analyzing or synthesizing chemical or biological products in conventional macroscopic volumes. Such tools include, for example: metering devices, reactors, valves, heaters, coolers, mixers, splitters, diverters, cannulas, filters, condensers, incubators, separation devices, and catalyst devices. Attempts to perform chemical or biological synthesis and/or analysis in microfluidic volumes have been stifled by difficulties in making tools for analysis and/or synthesis at microfluidic scale and then integrating such tools into microfluidic devices. Another difficulty is accurately measuring stoichiometric microfluidic volumes of reagents and solvents to perform synthesis on a microfluidic scale. Additionally, difficulties in rapidly prototypic microfluidic devices are compounded by attempts to incorporate multiple analysis and/or synthesis tools for multi-step analysis and/or synthesis.

When working with fluids in conventional macroscopic volumes, fluid metering is relatively straightforward. In microfluidic volumes, however, fluid metering is considerably more difficult. Most, if not all, microfluidic systems require some interface to the conventional macrofluidic world. Using conventional macrofluidic techniques, the smallest volume of liquid that can be generated is a droplet, typically ranging in volume between approximately 1–100 microliters. At the low end of this volumetric range it is extremely difficult to consistently create droplets having a reasonably low volumetric standard deviation. Applications in which fluidic metering accuracy is important include microfluidic synthesis, wherein it would be desirable to measure stoichiometric microfluidic volumes of reagents and solvents.

A known method of obtaining small droplets is to combine fluids to be metered with surfactants before dispensing the liquid through a pipet tip. But this method is unacceptable for many applications, since adding surfactants may detrimentally compromise the purity of the fluid to be metered, and it may be very challenging to remove the surfactants and purify the fluid for further processing or use.

It is further difficult to segregate a small fluid volume from a larger bulk volume within a microfluidic device. Such segregation requires the forces of cohesion (interaction between like fluid molecules) and adhesion (interaction between fluid molecules and the surrounding conduit) to be overcome. It is believed that the general dominance of surface effects over momentum effects in microfluidic systems contributes to the challenge of performing fluid metering within such systems.

Another known method for metering small volumes of fluids is to cause the fluid to flow into a receptacle at a particular flow rate for a particular period of time and integrate the flow rate over the time to determine the volume deposited in the receptacle. For example, a fluid flowing into a receptacle at a rate of one microliter per second for one second will yield a one microliter sample in the receptacle. PCT Patent Application Number WO-01/04909 A1, entitled "Fluid Delivery Systems for a Microfluidic Device Using a Pressure Pulse," by Orchid Biosciences, Inc. (the "Orchid Application"), discloses a system where a plurality of branches are filled with a fluid up to a capillary break. The capillary break prevents the fluid from flowing into the test cell until the fluid pressure exceeds the pressure required to overcome the impedance of the capillary break (the "break pressure"). A pressure pulse of predetermined duration and amplitude is provided to overcome the break pressure. The duration of the pressure pulse is selected so that the desired amount of fluid flows into the test cell. In other words, the pressure pulse causes the fluid to flow into the test cell at a given rate for a given period of time to provide the desired sample volume.

This approach may not achieve the desired accuracy because of hysteresis in the system resulting from the fluid compression and variations in fluidic impedance throughout the system. Moreover, inaccuracies may be amplified in larger systems where large numbers of receptacles, many at some distance from the pressure source, are served by a complex system of fluid conduits. Also, the behavior of the system may vary depending on the materials with which the device is constructed. It is known that microfluidic flow characteristics are largely the result of surface interactions between the fluid and the microfluidic conduit or chamber. Thus, different fluids may exhibit different flow properties within the same conduit. For example, an aqueous solution under a given pressure may flow more slowly than a non-aqueous solution in a hydrophobic conduit, with the reverse being true if the conduit material were hydrophilic. As a consequence of the differing flow characteristics, a pressure pulse driving a metering operation would have to be tailored to each type of material and fluid combination used in the device. However, a wide range of materials and fluids are desirable. For example, both hydrophobic and hydrophilic solvents frequently are used in analysis and synthesis operations. Also, solvents frequently have corrosive qualities that are incompatible particular conduit materials-and many solvents are incompatible with each other. Thus, a control system for a flow-rate/time based metering system would necessarily have a different control program for each possible fluid/material combination, and the introduction of new materials or fluids would require an updated control program that may require experimentation or empirical analysis to determine flow characteristics. The complexity of such a system would make it prone to operator error. Moreover, inadvertent contamination of the fluids or materials could significantly alter the accuracy of the equipment without the error being easily detected by the operator.

Accordingly, there exists a need for metering devices and methods capable of consistently metering fluids in microfluidic volumes while minimizing the need to accommodate variations in fluid flow and material properties.

SUMMARY OF THE INVENTION

In a first aspect of the invention, a method for metering a plurality of microfluidic plugs from a larger fluidic volume comprises the steps of providing a trunk channel having a fluidic outlet and a plurality of microfluidic branch channels, each having an associated fluidic impedance region. Each branch channel of the plurality of branch channels is in fluid communication with the trunk channel. A first fluid volume is supplied to the trunk channel. Each branch channel is filled, directly from the trunk channel, to each fluidic impedance region with a portion of the first fluid volume. A second fluid is used to flush the remaining portion of the first fluid from the trunk channel through the fluidic outlet while each branch channel remains substantially filled.

In another aspect of the invention, a method for metering a microfluidic plug from a larger fluidic volume comprises the steps of providing a trunk channel having a fluidic outletand a microfluidic branch channel having an associated fluidic impedance region. The branch channel is in fluid communication with the trunk channel. A first fluid volume is supplied to the trunk channel. The branch channel is filled, directly from the trunk channel, to the fluidic impedance region with a portion of the first fluid volume. A second fluid flushes the remaining portion of the first fluid from the trunk channel through the fluidic outlet while the branch channel remains substantially filled.

In another aspect of the invention, a device for metering a microfluidic plug of fluid from a larger fluidic volume comprises a trunk channel having a fluidic inlet and a fluidic outlet and a microfluidic branch channel in direct, independent fluid communication with the trunk channel. The branch channel has a fluidic impedance region. The trunk channel, branch channel, fluidic inlet, fluidic outlet, and fluidic impedance are arranged to permit a first fluid to be supplied through the trunk channel to fill the branch channel to the fluidic impedance region, and thereafter to permit the fluidic contents of the trunk channel to be flushed through the fluidic outlet while the branch channel remains substantially filled.

In another separate aspect of the invention, any of the foregoing separate aspects may be combined for additional advantage. These and other aspects and advantages of the invention will be apparent to the skilled artisan upon review of the following description, drawings and claims.

DETAILED DESCRIPTION OF PREFERRED EMBODIMENTS OF THE INVENTION

Definitions

The term "channel" or "chamber" as used herein is to be interpreted in a broad sense. Thus, it is not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flowthrough cell where fluid is to be continually passed or, alternatively, a chamber for holding a specified, discrete ratio of fluid for a specified ratio of time. "Channels" and "chambers" may be filled or may contain internal structures comprising, for example, valves, filters, and similar or equivalent components and materials.

The term "microfluidic" as used herein is to be understood to refer to structures or devices through which a fluid is capable of being passed or directed, wherein one or more of the dimensions is less than about five hundred microns or to fluidic volumes of less than or equal to about two microliters.

The term "microfluidic impedance" as used herein is to be understood, without any restriction thereto, to refer to structures within the microfluidic device that hinder fluid flow. The shape, geometry and material that comprise these devices are not limited to the specific examples provided herein.

The terms "positive pressure" and "negative pressure" as used herein refer to pressures differing from a reference pressure. A preferred reference pressure is atmospheric pressure.

The term "plug" as used herein refers to a discrete portion of fluid typically separated from a larger volume.

The term "self-adhesive tape" as used herein refers to a material layer or film having an integral adhesive coating on one or both sides.

The terms "stencil" or "stencil layer" as used herein refers to a material layer or sheet that is preferably substantially planar, through which one or more variously shaped and oriented channels have been cut or otherwise removed through the entire thickness of the layer, thus permitting substantial fluid movement within the layer (as opposed to simple through-holes for transmitting fluid through one layer to another layer). The outlines of the cut or otherwise removed portions form the lateral boundaries of microstructures that are completed when a stencil is sandwiched between other layers, such as substrates and/or other stencils. Stencil layers can be either substantially rigid or flexible (thus permitting one or more layers to be manipulated so as not to lie in a plane).

Microfluidic Devices Generally

In an especially preferred embodiment, microfluidic devices according to the present invention are constructed using stencil layers or sheets to define channels and/or chambers. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filter materials. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. Specific examples of methods for directly bonding layers of non-biaxially-oriented polypropylene to form stencil-based microfluidic structures are disclosed in copending U.S.

Provisional Patent Application Serial No. 60/338,286 (filed Dec. 6, 2001), which is owned by assignee of the present application and incorporated by reference as if fully set forth herein. In one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately 5 hours at a temperature of 154° C. to yield a permanently bonded microstructure well-suited for use with high-pressure column packing methods.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Preferred Embodiments

Microfluidic devices and methods for metering discrete plugs (also called aliquots) of fluid in accordance with the present invention provide a trunk channel and a microfluidic branch channel having an impedance. The fluidic impedance region may be or include an overlap, a porous material, a passive valve, an active valve, a constriction in the channel or any other suitable means for impeding flow of the fluid from the branch channel. A fluid is supplied to the trunk channel and fills the branch channel to the impedance region. The fluid is then flushed from the trunk channel leaving the branch channel filled. Because the branch channel has a volume, a discrete plug of the fluid having a volume equal to that of the branch channel is formed. The device may be designed to provide a branch channel with a desired volume, thus providing precisely metered fluid plugs of that desired volume.

In a preferred embodiment the fluid provided to the trunk and branch channel is a liquid, and the flushing step is performed with a gas. The fluid remaining in the branch channel may be subsequently removed, such as by generating a pressure differential between the branch channel and an external region. In a preferred embodiment the first fluid provided to the trunk and branch channel is a liquid, and the flushing step is performed with a second fluid, which is a gas. Alternatively, the second fluid may be another liquid that is substantially immiscible with the first fluid. In another embodiment, the first fluid may be a gas and the second fluid a liquid. In other words, any combination of fluids may be used, so long as the first fluid and the second fluid are substantially immiscible. Of course, if the diffusion mixing rate between the fluids is very slow and the metering operation is performed relatively quickly, little or no diffusion mixing may occur, thus permitting the use of otherwise miscible fluids. For example, the second fluid may a gas that is soluble in the first fluid, provided that the rate at which the gas goes into solution with the first fluid, particularly given the extremely small fluid/gas interface are, is very slow relative to the duration of the metering operation. In another embodiment, a first fluid is supplied to the trunk channel and thereafter flushed from the trunk channel into a reservoir for retaining the excess fluid.

The plugs of the first fluid remaining in the branch channels may be subsequently removed, such as by generating a pressure differential between the branch channel and an external region. In one embodiment, a microfluidic device consists of one or more microfluidic channels that are located on different layers of a three dimensional device. The channels are overlapped in certain areas in order to create fluidic impedances. Fluidic impedances hinder fluid flow through the device. The shape and the amount of overlap in the impedance can be controlled in order to alter the differential pressure necessary to cause fluid to flow through the impedance.

In a preferred embodiment, the differential pressure is increased by externally applying pressure. The channels and chamber within a microfluidic device can have outlet connections, so an off-board manifold system can be used. The manifold can connect to the inlet and outlet ports of the microfluidic device and switch pressure on and off of these ports in order to provide pressure to the channels when necessary. In one embodiment, this manifold might consist of a valving system that is connected at one end to a nitrogen tank, or other pressurized system. The valving system could be controlled to selectively apply the pressurized nitrogen to the channels of the device. This system could be controlled manually, or by a computer or other built in controller. Additionally, feedback to the valving system could be used for this control. Sensors may be used to monitor the fluid flow within the device. When the fluid reaches a certain point, the valving system could be automatically switched as per a given protocol.

Figure 1A:
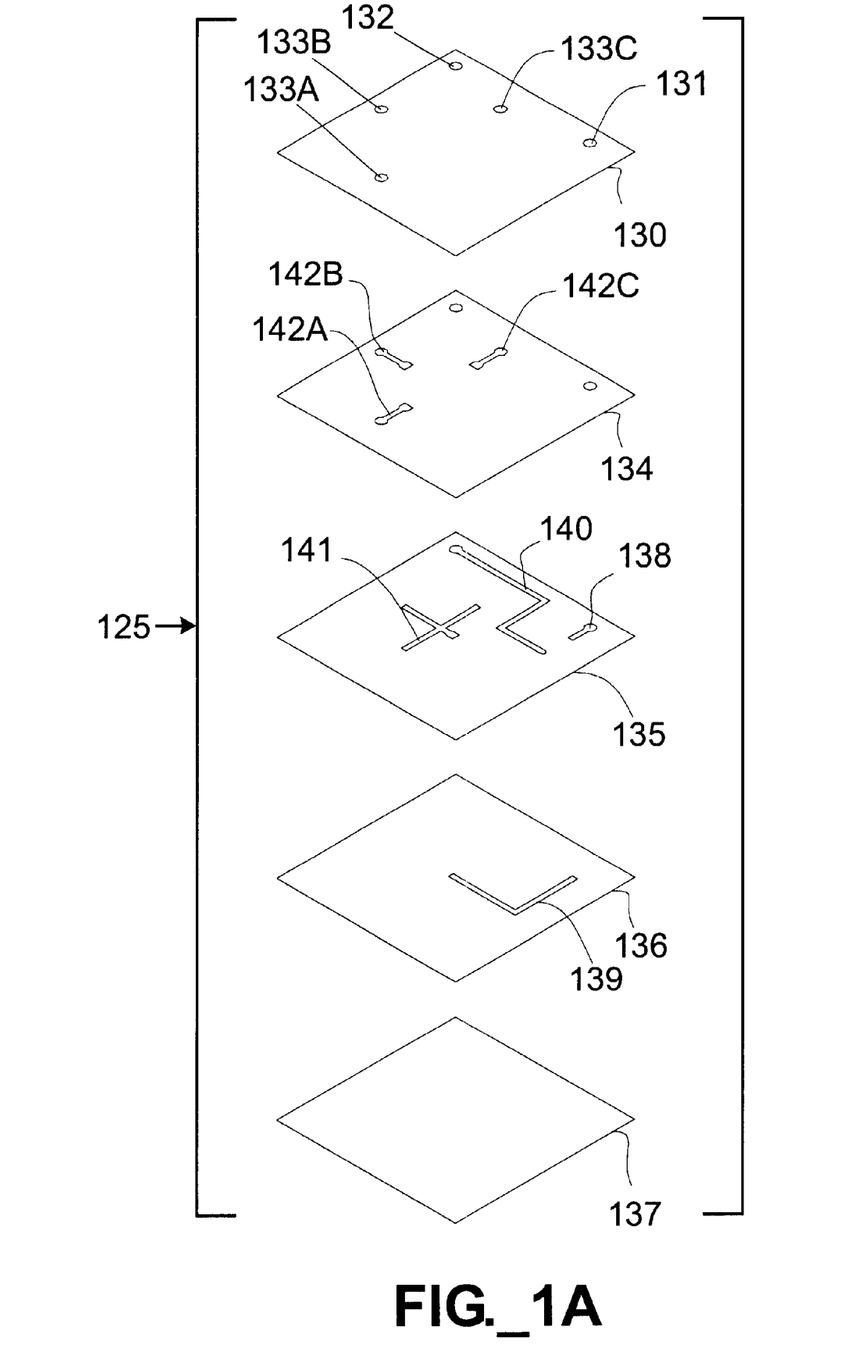
FIG. 1A is an exploded perspective view of a multi-layer, three-dimensional microfluidic device according to one embodiment of the present invention.
Figure 1B:
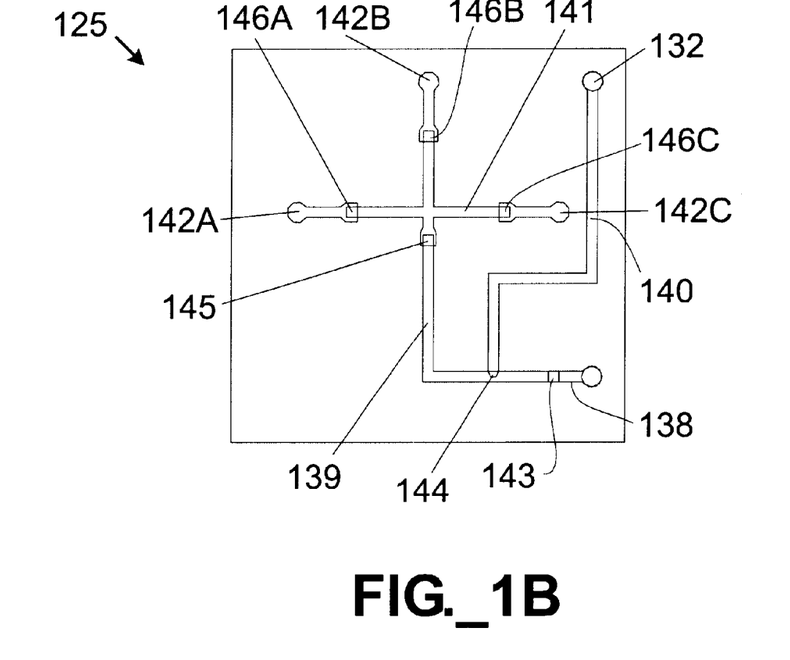
FIG. 1B is a top view of the assembled device of FIG. 1A.

FIGS. 1A–1B illustrate a microfluidic device 125 according to the invention. The microfluidic device 125 brings in a quantity of sample that has a large standard deviation, meters a known amount with a smaller standard deviation, divides the metered amount into three equal components, and brings the sample off-board for further analysis.

Referring to FIG. 1A, an inlet port 131, control port 132, and outlet ports 133A–133C were created in a one eight inch thick polycarbonate base 130. Four device layers were created 134–137, including stencil layers 134–136 which defined channels 138–142. In this example, single sided pieces of tape consisting of three mil (seventy-six micron) polypropylene backing with permanent water based adhesive were used as the device layer material. The device layers 134–137 were adhered together and onto the polycarbonate base. The assembled device is shown in FIG. 1B and contains four different types of overlap regions 143–145, 146A–146C. All of the channels 138–142 are three mils (seventy-six microns) high, thus the overlap regions are six mils (one hundred and fifty-two microns) combined. At overlap 143, both channels 138,139 are forty mils (one thousand microns) wide and they overlap for forty mils (one thousand microns). At overlap 144, waste channel 140 is forty mils (one thousand microns) wide and tapers down to twenty mils (five hundred microns) in the overlap region;

channel 139 is forty mils (one thousand microns) wide and waste channel 140 extends across 139 for 20 mils (five hundred microns). Overlaps 145 and 146 are identical. The entry channels 139,141 are forty mils (one thousand microns) wide, the exit portions 142A–142C are seventy mils (eighteen hundred microns) wide and the overlap is forty mils (one thousand microns) in length.

In operation, a sample plug is injected at the inlet port 131 using a syringe pump or any other fluid supply capable of providing a constant flow rate and pressure. A first fluidic impedance 143 is constructed immediately after the inlet port 131 to control the initial fluid flow. The fluid then passes into a channel 139 and fills the channel 139 until it reaches a second impedance 145. At this point, the excess fluid within the sample breaks through a third impedance 144 before breaking the second impedance 145. Thus, any excess fluid passes down the waste channel 140. Once all of the excess fluid has been sent to the waste channel 140, the control port 132 can be plugged to increase the pressure within the channels. The amount of sample now ready for further analysis is defined by the volume of channel 139 between the second and third impedances 144,145. If a different sample volume is desired, the microfluidic impedance 144 can be moved along channel 139 to alter the volume.

Once the air in channel 140 has been compressed sufficiently to build up enough pressure, the second impedance 145 is overcome. The sample now enters chamber 141 and fills the entire chamber up to three fourth impedances 146A–146C. Once this chamber 141 has been completely filled, the fourth impedances 146A–146C are overcome and the samples can now be exported off the device for further analysis. In certain embodiments, the output holes 133A–133C are countersunk and a capillary is inserted into the holes. The countersinks are adjusted to create a tight fit around the capillaries. Although channel 140 is referred to in this illustrative embodiment as a "waste" channel, it will be understood by one skilled in the art that the combination of the waste channel 140, the inlet channel 138, and the portion of the channel 139 between the inlet 138 and the second impedance 144 are, in essence, the "trunk" of the trunk and branch channel approach associated with the invention. Of course the same applies to the devices shown in FIGS. 2A–2B, with respect to channels 155, 156, and 158 and impedance 166, and FIGS. 3A–3B, with respect to channels 412A, 412B and 416 and impedance 418A, discussed below.

Figure 2A:
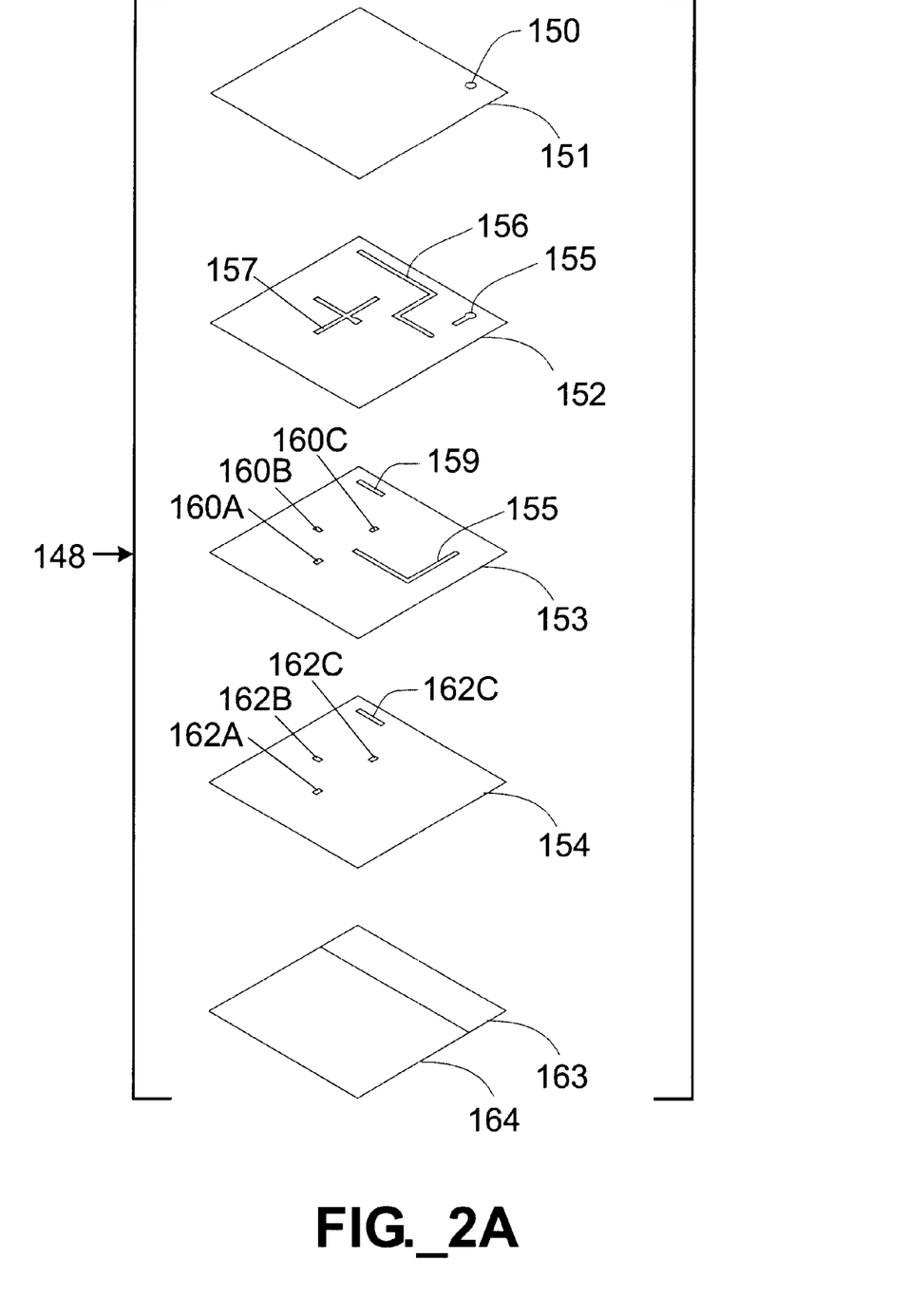
FIG. 2A is an exploded perspective view of a multi-layer, three-dimensional microfluidic device according to another embodiment of the present invention.
Figure 2B:
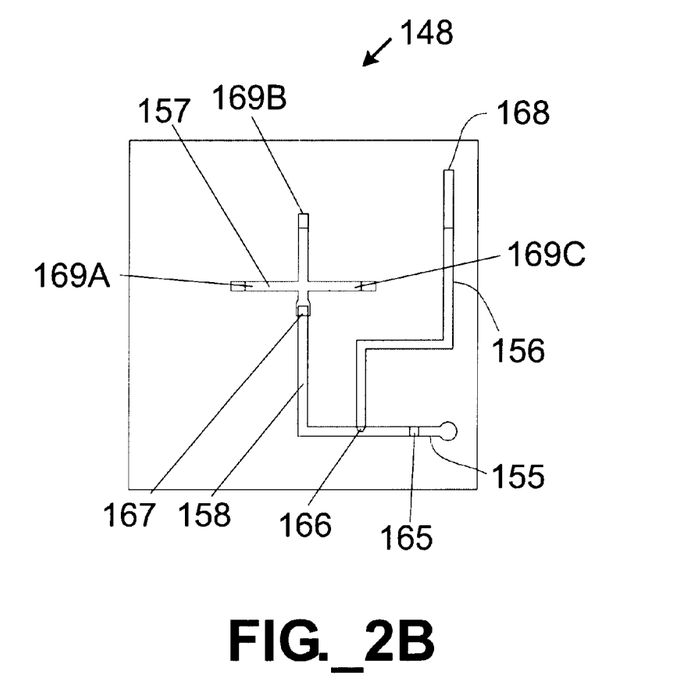
FIG. 2B is a top view of the assembled device of FIG. 2A.

FIGS. 2A–2B illustrates a microfluidic device 148 according to the invention wherein all of the metering occurs automatically with a built-in valving system. A detection technology can be added to the device 148 to analyze the metered samples.

Referring to FIG. 2A, an inlet port 150 was created in a ⅛" thick polycarbonate base 151. Three stencil layers 152–154 were created that have channels 155–158 and chambers 159–162 cut into them. Two of the stencil layers, 152, 153 were constructed from single sided polypropylene tape with a permanent water-based adhesive having a total thickness of three mils (seventy six microns). The other stencil 154 was constructed from double-sided tape (0.5 mil (12.6 micron) thick polyester carrier with 1.8 mil (46 micron) thick acrylic adhesive on each side). The stencil layers 152–154 were adhered together and onto the polycarbonate base 150. Two different types of porous material were adhered to stencil layer 154. Material 163 is polytetrafluoroethylene having an average pore size of 30–60 microns and covers the chamber 161. The other porous material 164 is ultra high molecular weight polyethylene having an average pore size of 2.5–4.5 microns and covers the outlet channels 160A–160C, 162A–162C. The assembled device 148, shown in FIG. 2B, contains three types of overlap regions 165–167 and two types of outlet channels 168, 169A–169C.

In operation, a fluid plug is injected into the inlet port 150. The fluid enters the device and passes across a first microfluidic impedance 165. The fluid fills the channel 158 past a second microfluidic impedance 166 until it reaches a third microfluidic impedance 167. At this point, the fluid now encounters two impedances 166, 167. In order for the fluid to continue to flow, air must be pushed through one or both of the porous materials 163, 164 at the outlets 168 and/or 169A–169C. In this example, material 163 covering outlet channel 168 is chosen to have a smaller pressure drop across than that across the material 164 covering outlet channels 169A–169C. Thus, the second microfluidic impedance 166 is overcome first. The excess of the fluid sample passes into the waste channel 156 until the front reaches the interface of the porous material 163. At this point, the system would prefer to pass air across the material 164 than liquid across material 163. The microfluidic impedance at 167 then is overcome. The fluid sample volume, which equals the volume of channel 158 from the second and third microfluidic impedances 166, 167 is split equally into the sample channels 157A–157C. Detection technology can be added to the sample channels 157A–157C for on board analysis of the samples.

The volume of the channels may be adjusted to accommodate various sample sizes. Because of errors in delivering small volumes of samples, sample injection volumes can have substantial variability within a range from a high end to a low end. Importantly, the volume of sample area (within 158) must be smaller than the low end of the sample volume injected. Additionally, the volume of channel 156 and chambers 159 and 161 must be greater than the high end of the sample volume injected. For example, for a sample injection volume of one microliter, plus or minus thirty percent, the volume of chamber 158 between the two microfluidic impedances (166 and 167) must be less than seven hundred nanoliters. Additionally, the volume of 156, 159, and 161 must be greater than the total possible volume, thirteen hundred nanoliters minus the sample volume. In a preferred embodiment, the metering volume would be six hundred nanoliters and the waste system would be one microliter. Of course, this approach to determining the desired volumes of each component may be applied to any embodiment of the invention disclosed herein and any other embodiment that may be apparent to one skilled in the art.

Figure 3A:
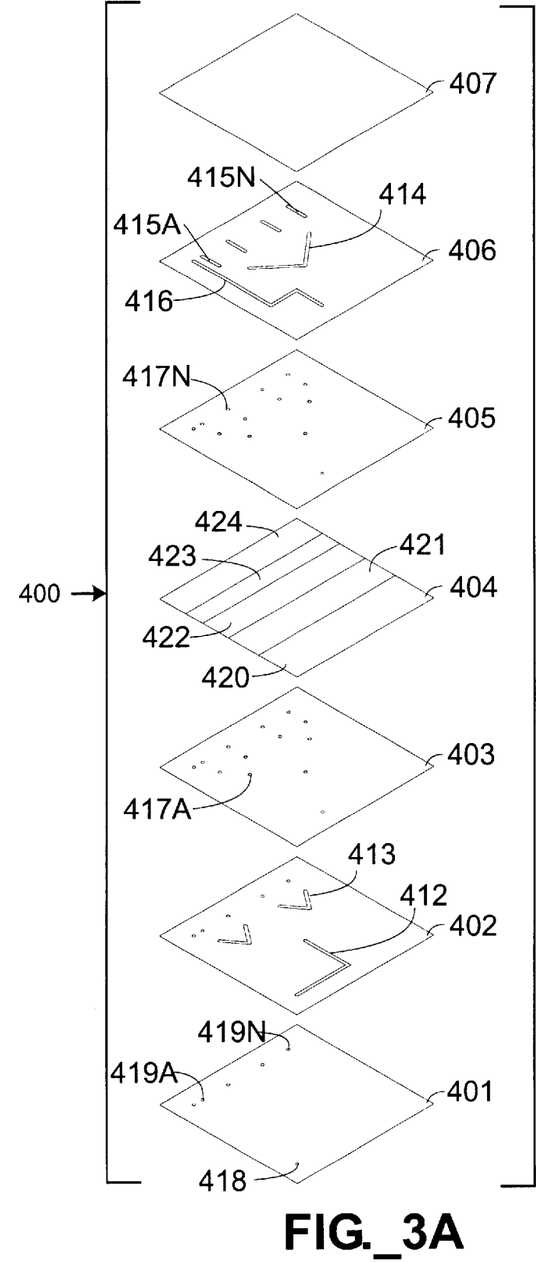
FIG. 3A is an exploded perspective view of a multi-layer, three-dimensional microfluidic device according to another embodiment of the present invention.
Figure 3B:
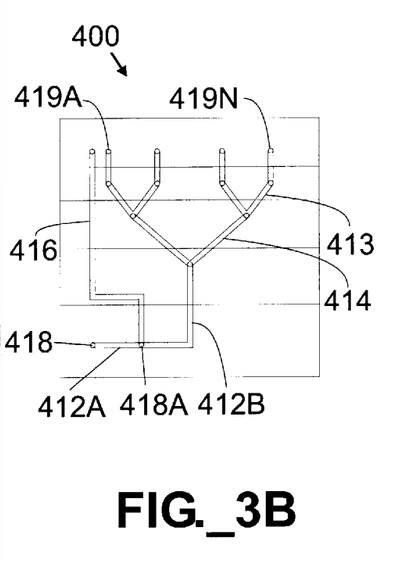
FIG. 3B is a top view of the assembled device of FIG. 3A.

In another embodiment, porous membrane valves can be used in a device to create a microfluidic metering system. Referring to FIG. 3A, an exploded view of a microfluidic device 149 is shown that was constructed from seven device layers 401–407, including two stencil layers 402, 406. Defined in the device layers are channels 412–416, vias 417A–417N, an entry port 418, and, branch channel 414, sub-branch channels 413, 415A–415N, exit ports 419A–419N. (Although FIGS. 3A–3B show a device 400 with four sub-branch channels 415A–415N, it will be readily apparent to one skilled in the art that any number of branch channels may be provided. For this reason, the designation "N" is used to represent the last branch channel 415N, with the understanding that "N" represents a variable and could represent any desired number of branch channels. This convention is used throughout this document.) Device layer 404 is constructed from five different porous materials to provide a plurality of porous regions 4204–424, one or more of which may differ in porosity from the others. Porous region 420 is 40-micron pore size UHMWPE, porous region 421 is 30-micron pore size UHMWPE, porous region 422 is 20-micron pore size UHMWPE, porous region 423 is 10-micron pore size UHMWPE, and porous region 424 is 1-micron pore size UHMWPE. Device layers 403 and 405 are constructed from single- sided adhesive tape with the adhesive facing device layer 404, stencil layers 402 and 406 are double sided adhesive tape, and device layers 401 and 407 are polymeric films with no adhesive. For examples of the materials that can be used, see U.S. patent application Ser. No. 09/453,029, the entirety of which is incorporated herein by this reference.

The assembled device 400 is shown in FIG. 3B. In use, a small portion of fluid is injected at the entry port 418 and passes down channel 412 until it reaches the end of the channel. The portion of fluid should be large enough to fill the metering portion of channel 412, but not greater than the total volume of channels 412 and 416. The excess fluid then passes through porous region 420 into waste channel 416 since the pressure drop across porous region 420 is the weakest of the five porous regions 420–424. Air is injected behind the fluid to drive the flow. Once the waste fluid reaches the end of channel 416, the fluid in channel 412 passes through porous region 421, since the pressure drop across porous region 421 is weaker than the drop across porous region 424 at the exit of the channel 416. The plug of fluid passes through porous region 421 and then is split equally in multiple channels 414. The volume of each channel 414 is exactly one-half the volume of the metering portion of channel 412. Once channel 414 is filled, the two plugs of fluid pass through porous region 422 and enter into channels 413. Each channel 413 is exactly one-quarter of the volume of channel 412. Once each channel 413 is filled, the fluid passes through porous region 423 and goes to the exit ports 419A–419N through channels 415A–415N. In summary, this device 400 takes an uncertain volume of fluid, meters off a known amount, and splits that sample into four equal portions or plugs for further analysis. The porous membrane regions control the fluidic pathway in the device.

In a preferred embodiment, different porous membranes can be used to control the flow rate (and therefore total volume) down a given channel. At a given backpressure, membranes of different porosities and void volumes will have different flow-through rates. Many factors can affect the profile of fluid flow rate versus backpressure for flow through a given porous material. These factors include, but are not limited to, the chemical nature of the membrane, pore size of the membrane, geometry and shape of the pores in the membrane, amount of surface area of the membrane, size of the opening where the fluid will flow through, and other parameters. The nature of the fluid that is flowed will also have an effect. Fluid factors include but are not limited to composition of the fluid, surface tension of the fluid, viscosity of the fluid, temperature, and compressibility of the fluid.

The devices shown in FIGS. 1A–1B, 2A–2B, and 3A–3B are, however, limited in two respects. First, there is a single primary branch channel fed by the trunk channel. The desired number of fluid samples are created by subdividing the fluid in the primary branch channel into sub-branch channels. Because two fluid subdivisions take place, the opportunity for error may be increased. Second, the number of fluid samples provided by such devices may be limited by the number and size of features that can be defined within the device. In other words, there is a physical limit to the number of sub-branch channels that can be fed by a single primary branch channel. Each of the illustrated devices are shown with three sub-branch channels, and, although one skilled in the art could create a similar design with six, eight or more sub-branch channels, at some point the number of sub-branch channels would be limited by the amount of physical space available around the primary branch channel. Moreover, as the number of sub-branch channels increase, the volume (and hence the length, depth, and/or width) of the primary branch and trunk channels must increase to accommodate the amount of fluid required to provide the samples, together with accommodation for sample error (as discussed above). If too many sub-branch channels are desired, the required volume of the primary branch and trunk channels may exceed microfluidic proportions, thus eliminating the desired fluidic behavioral characteristics. Alternatively, the primary branch and trunk channels could be convoluted to increase their length without altering the microfluidic dimensions of the cross-section of the channels, however excessive convolutions could substantially complicate the manufacturing process of the device, as well as increasing the footprint of the device (thus eliminating one advantage of microfluidic devices—i.e., small size).

Figure 4A:
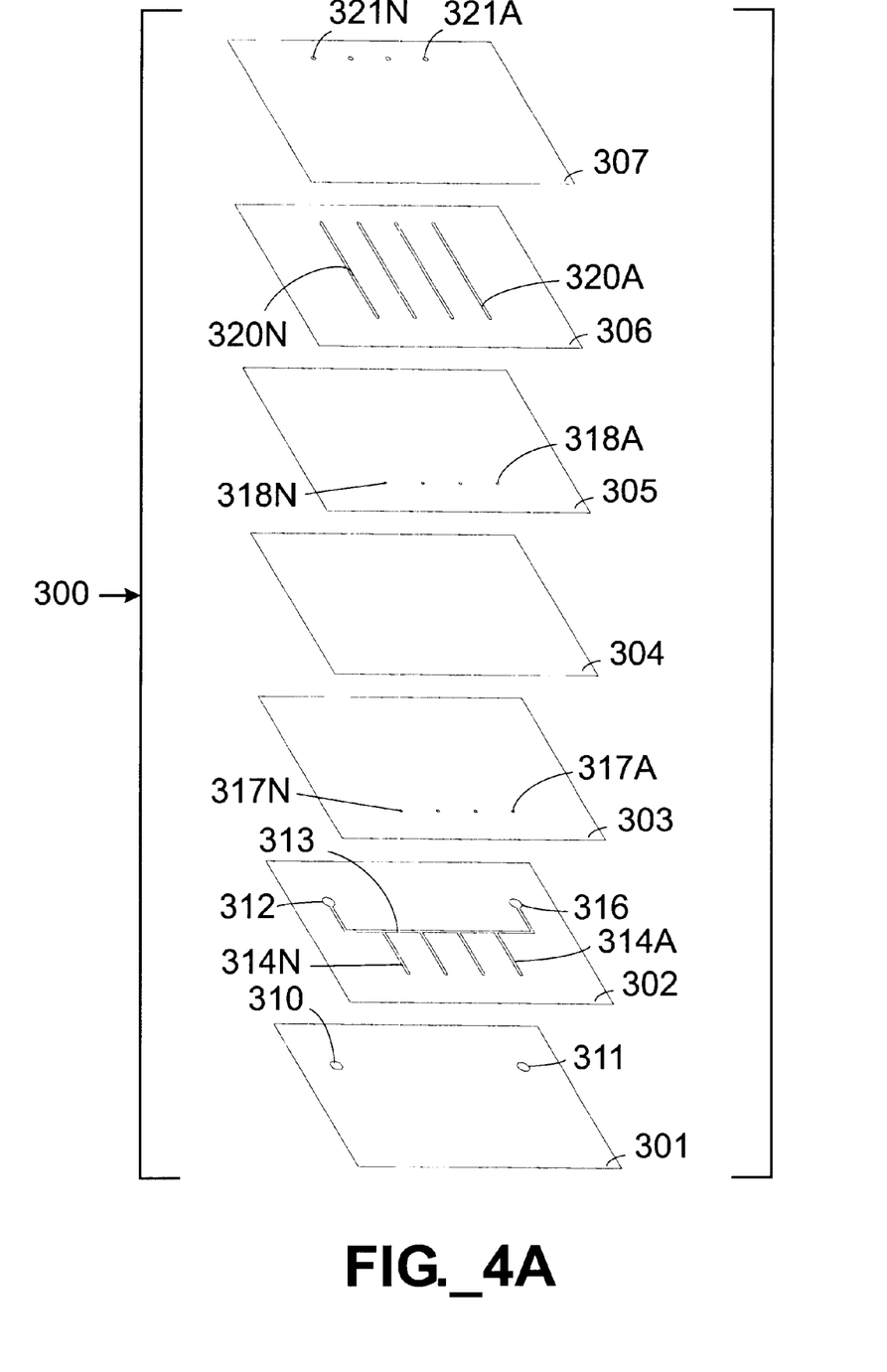
FIG. 4A is an exploded perspective view of a multi-layer, three-dimensional microfluidic device according to another embodiment of the present invention.
Figure 4B:
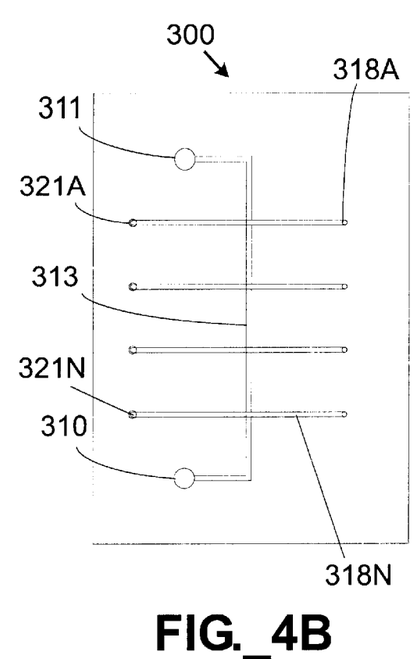
FIG. 4B is a top view of the assembled device of FIG. 4A.

In another embodiment, a direct trunk-branch metering method may be used to meter microfluidic quantities of fluid from a larger fluidic volume. For example, referring to FIGS. 4A–4B, a fluidic metering device 300 is constructed in seven device layers 301–307, including stencil layers 302, 306. Starting from the bottom of the device 300, the first layer 301 defines a fluidic inlet port 310 and outlet port 311 in communication with either end 312, 316 of a trunk channel 313 in the second layer 302. Within the second layer 302, several branch channels 314A–314N in fluid communication with the trunk channel 313 are provided. (Although FIGS. 4A–4B show a device 300 with four branch channels 314A–314N, it will be readily apparent to one skilled in the art that any number of branch channels may be provided. For this reason, the designation "N" is used to represent the last branch channel 314N, with the understanding that "N" represents a variable and could represent any desired number of branch channels.) The third layer 303 defines vias 317A–317N aligned with the ends of the branch channels 314A–314N in the second layer 302. The fourth layer 304 is a porous membrane that inhibits fluid flow at low pressures but permits fluid to pass at higher pressures. For example, if the first fluid is an aqueous solution, then the fourth layer may be fabricated with five-mil (about one hundred twenty-five micron) porous UHMW polyethylene with three point five micron pores (DeWal Industries "DW 402FP," Saunderstown, RI). The fifth layer 305 defines vias 318A–318N aligned with the vias 317A–317N located in the third layer 303, and the fifth layer vias 318A–318N provide a fluidic path to channels 320A–320N defined in the sixth layer 306. The seventh layer 307 covers the channels 320A–320N in the sixth layer 306 and provides outlet ports 321A–321N disposed at the ends of the channels 320A–320N. A wide variety of materials may be used for the other layers. In a preferred embodiment, one or more of the layers are constructed from polymeric materials. In an especially preferred embodiment, one or more layers are fabricated from self-adhesive materials. Of course, the porous fourth layer 304 is preferably fabricated from a permeable or porous material, although any material may be used provided a porous portion is provided between the porous regions aligned with the vias 317A–317N, 318A–318N.

In operation, a first fluid of indeterminate volume is supplied through the inlet port 310 and via 312 to the trunk channel 313. From the trunk channel 313, the first fluid fills all of the branch channels 314A–314N before any surplus first fluid exits the device 300 by way of via 316 through the outlet port 311. Thereafter, a second fluid is supplied to the trunk channel 313, such as by manipulating external valves (not shown) to direct the second fluid into the inlet port 310. Preferably (but not necessarily) the first fluid and second fluid are substantially immiscible. A first stream of second fluid provided at a low pressure serves to push or flush the first fluid out of the trunk channel 313, but does not disturb the plugs of first fluid remaining in the branch channels 314A–314N. The volume of each of the plugs is approximately equal to the volume of each branch channel 314A–314N. Following the flushing step, the pressure of the second fluid is increased to force the plugs of first fluid upward through the porous membrane 304 by way of the vias 317A–317N, 318A–318N into the channels 320A–320N located in the sixth layer 306. Thus, the plugs of first fluid are removed from the branch channels 314A–314N by virtue of a pressure differential between each branch channel 314A–314N and another region. From the channels 314A–314N, the first fluid may be pushed toward (and ultimately through) the outlet ports 321A–321N, such as for further processing or analysis. Pressure of the second fluid within the trunk channel 313 may be increased, for example, by closing an external valve (not shown) downstream of the outlet port 311 and then increasing the supply pressure of the second fluid. While the second fluid may be most any liquid or gas, it is preferably a gas, and is more preferably an inexpensive and/or inert gas such as air, nitrogen, carbon dioxide, or argon, although other gases may be advantageously used. The first fluid is preferably a liquid, especially in the device 300 shown in FIGS. 4A–4B where a gas-permeable porous region is used to impede the passage of fluid at the end of each branch channel. More preferably, the first fluid is a substantially pure liquid, meaning that it is substantially free of additives or surfactants that might detrimentally interfere with further use or analysis of microfluidic plugs of the liquid. Notably, use of the porous membrane in the fourth layer 304 also aids in filling the branch channels 314A–314N with the first fluid by providing a route for any air entrained in the branches 314A–314N to be displaced ahead of the incoming fluid.

In an alternative embodiment (not shown), active valves that provide sealing capability against gas flow may be substituted for the porous impedance regions provided in the device 300. One example of a type of active valve that could be used is a flexible membrane that is locally deformed by air pressure to seal fluidic passages. Such an alternative embodiment would, for example, permit the first fluid to be either a liquid or a gas. Since gas is compressible, however, substantially more volumetric uncertainty would result if the desired metering product was in gas phase.

Figure 5A:
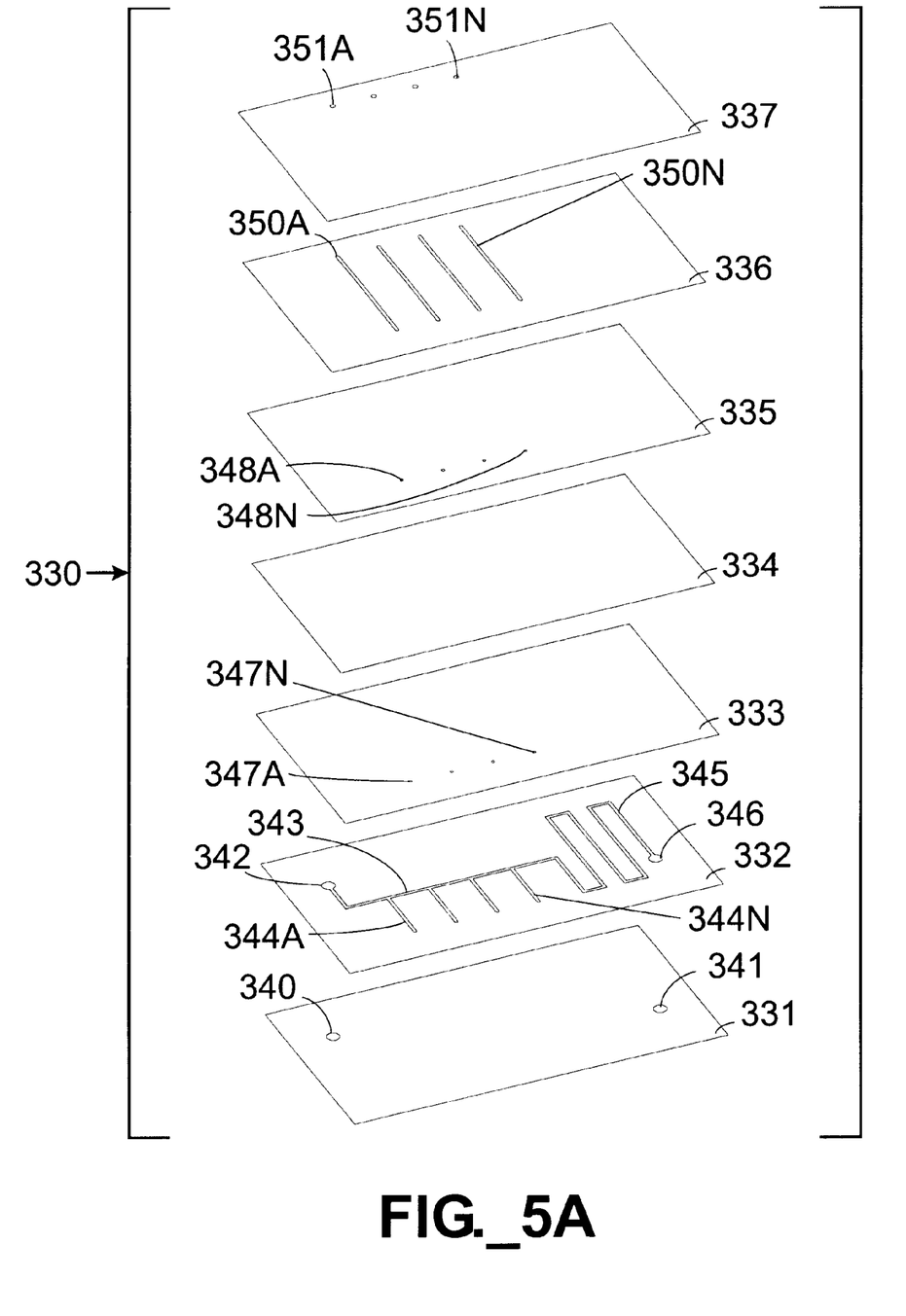
FIG. 5A is an exploded perspective view of a multi-layer, three-dimensional microfluidic device according to another embodiment of the present invention.
Figure 5B:
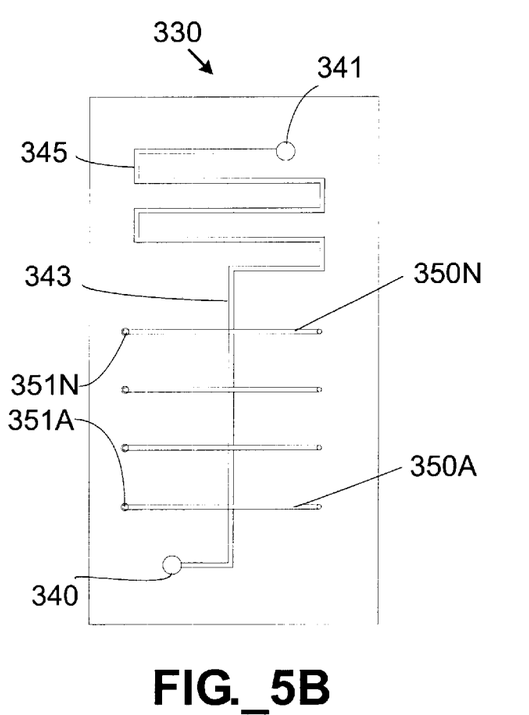
FIG. 5B is a top view of the assembled device of FIG. 5A.

Another embodiment similar to that provided in FIGS. 4A–4B and utilizing a trunkbranch metering method to meter fluids is illustrated in FIGS. 5A–5B. In this example, a microfluidic metering device 330 is constructed in seven device layers 331–337, including stencil layers 332, 336. As before, the first layer 331 defines an inlet port 340 and outlet port 341. The second layer 332 defines a trunk channel 343, several branch channels 344A–344N, a serpentine reservoir channel 345 for collecting surplus fluid, and vias 342, 346 communicating with the trunk channel 343. The reservoir channel 345 is the primary difference between this device 330 and the device 300 illustrated in FIGS. 4A–4B. The third and fifth layers 333, 335 define vias 347A–347N, 348A–348N aligned with the ends of the branch channels 344A–344N, with a porous membrane used as the fourth layer 334. The sixth layer 336 defines several channels 350A–350N leading to outlet ports 351A–351N defined in the seventh layer 337. Operation of the device 330 is similar to that of the device 300 in the previous example, except for the steps of filling and flushing the trunk channel 343. Here, a first fluid is supplied through the inlet port 340 to the trunk channel 343 and fills the branch channels 344A–344N as it progresses through the device 330. After the branch channels 344A–344N are filled, the first fluid remaining in the trunk channel 343 adjacent to the branch channels 344A–344N may be flushed completely out of the device 330 through the serpentine reservoir channel 345, via 346, and outlet port 341, or may alternatively just be flushed past the branches 344A–344N into the reservoir channel 345. In the latter case, surplus first fluid may remain in the reservoir channel 345 while the plugs of first fluid are forced through the porous membrane 334 so long as sufficient outlet resistance is provided ahead of the surplus first fluid—such as may be accomplished by closing an external valve (not shown) in communication with the outlet port 341. In an alternative embodiment, a reservoir for surplus fluid may be configured as one or more chambers rather than a serpentine channel. One utility of providing a reservoir for surplus first fluid is to preserve the surplus for further use, such as may be desirable when the fluid is particularly valuable and/or only a limited quantity of first fluid is available. This occurs frequently when manipulating fluids such as purified DNA or genomic materials, for example. In whatever application, the surplus fluid remaining in the reservoir may be extracted for further storage, use, or processing.

It should be noted that in devices 300 and 330, each branch channel 314A–314N, 344A–344N is fed directly from the trunk channel 313, 343. This approach avoids the need for a primary branch channel feeding sub-branch channels. Thus, the volume matching concerns addressed above with respect to the devices shown in FIGS. 1A–1B, 2A–2B, and 3A–3B are obviated. Moreover, this device is not constrained by geometric limits—any number of branch channels may be added to the system merely by extending the length of the trunk channel and ensuring the fluid supply is adequate to fill each of the branch channels. Consequently, while the sub-branching devices of FIGS. 1A–1B, 2A–2B, and 3A–3B may be suitable for delivering a limited number of samples, the direct-branching approach (i.e., where each branch channel is fed directly from the trunk channel and independently of any other branch channel), shown in FIGS. 4A–4B and 5A–5B, may be preferable for metering large numbers of samples. Of course, a single device (not shown) could include both sub-branching and direct-branching structures.

Generally, branch channels having various volumes may be constructed by altering the channel dimensions using any of a number of different fabrication methods. If, for example, a sandwiched stencil fabrication method is used, and the desired branch channel is straight with a rectangular cross-section, then the channel volume is merely the product of channel length, width, and height. Channels having a height of approximately fifty microns may be cut in a double-sided self-adhesive film having a carrier thickness of approximately twenty-five microns and adhesive approximately twelve-point-five microns thick on each side, and then sandwiched between adjacent layers. Branch channel volumes between fifty nanoliters and one microliter or larger may be defined in the above-mentioned fifty micron-thick double-sided film, as follows: cutting a channel two centimeters long by one millimeter wide yields a volume of one microliter; a channel four millimeters long by five hundred microns wide yields a volume of one hundred nanoliters; and a channel four millimeters long by two hundred and fifty microns wide yields a volume of fifty nanoliters. More complex channels, and channels having larger or smaller volumes may be constructed. Preferably, each branch or sub-branch channel has a volume of less than or equal to about two microliters; more preferably, each branch channel has a volume of less than or equal to about one microliter. In particular applications, each branch channel has a volume of less than or equal to about five hundred nanoliters.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. A method for metering a plurality of microfluidic plugs from a larger fluidic volume, the method comprising the steps of:
    providing a trunk channel having a fluidic outlet;
    providing a plurality of microfluidic branch channels, each having an associated fluidic impedance region, wherein each branch channel of the plurality of branch channels is in fluid communication with the trunk channel;
    supplying a first fluid volume to the trunk channel;
    filling, directly from the trunk channel, each branch channel of the plurality of branch channels to each fluidic impedance region with a portion of the first fluid volume; and
    flushing, with a second fluid, a remaining portion of the first fluid from the trunk channel through the fluidic outlet while each branch channel of the plurality of branch channels remains substantially filled.

2. The method of claim 1 wherein each branch channel of the plurality of branch channels is in independent, direct fluid communication with the trunk channel.

3. The method of claim 1 wherein the first fluid and the second fluid are substantially immiscible.

4. The method of claims 1 wherein the second fluid is a gas.

5. The method of claim 1 wherein any branch channel of the plurality of branch channels has a volume of less than about two microliters.

6. The method of claim 1 wherein any branch channel of the plurality of branch channels has a volume of less than about one microliter.

7. The method of claim 1 wherein any branch channel of the plurality of branch channels has a volume of less than about five hundred nanoliters.

8. The method of claim 1 further comprising the step of expelling the portions of the first fluid from the plurality of branch channels by generating a pressure differential.

9. The method of claim 1 wherein at least one fluidic impedance region includes a valve.

10. The method of claim 1 wherein at least one fluidic impedance region includes an overlap region.

11. The method of claim 1 wherein at least one fluidic impedance region includes a porous membrane.

12. The method of claim 11 wherein the porous membrane includes a plurality of porous regions.

13. The method of claim 1 wherein any branch channel of the plurality of branch channels has an associated gas-permeable vent.

14. The method of claim 1 wherein the trunk channel is a microfluidic channel.

15. The method of claim 1 wherein the trunk channel is in fluid communication with a reservoir, the method further comprising the step of receiving the first fluid flushed from the trunk channel in the reservoir.

16. The method of claim 15 wherein the reservoir comprises a microfluidic channel.

17. A method for metering a microfluidic plug from a larger fluidic volume, the method comprising the steps of:
    providing a trunk channel having a fluidic outlet;
    providing a microfluidic branch channel having an associated fluidic impedance region, wherein the branch channel is in fluid communication with the trunk channel;
    supplying a first fluid volume to the trunk channel;
    filling, directly from the trunk channel, the branch channel to the fluidic impedance region with a portion of the first fluid volume; and
    flushing, with a second fluid, a remaining portion of the first fluid from the trunk channel through the fluidic outlet while the branch channel remains substantially filled.

18. The method of claim 17 wherein the branch channel includes a plurality of microfluidic sub-branch channels, each having an associated sub-branch fluidic impedance region, wherein each sub-branch channel of the plurality of sub-branch channels is in fluid communication with the branch channel, the method further comprising the step of:
    filling, from the branch channel, each sub-branch channel of the plurality of sub-branch channels to each sub-branch fluidic impedance region with a sub-portion of the portion of the first fluid volume.

19. The method of claim 17 wherein the first fluid and the second fluid are substantially immiscible.

20. The method of claims 17 wherein the second fluid is a gas.

21. The method of claim 17 wherein the branch channel has a volume of less than about two microliters.

22. The method of claim 17 wherein the branch channel has a volume of less than about one microliter.

23. The method of claim 17 wherein the branch channel has a volume of less than about five hundred nanoliters.

24. The method of claim 17 further comprising the step of expelling the portion of the first fluid from the branch channel by generating a pressure differential.

25. The method of claim 17 wherein the fluidic impedance region includes a valve.

26. The method of claim 17 wherein the fluidic impedance region includes an overlap region.

27. The method of claim 17 wherein the fluidic impedance region includes a porous membrane.

28. The method of claim 27 wherein the porous membrane includes a plurality of porous regions.

29. The method of claim 17 wherein the branch channel has an associated gas-permeable vent.

30. The method of claim 17 wherein the trunk channel is a microfluidic channel.

31. The method of claim 17 wherein the trunk channel is in fluid communication with a reservoir, the method further comprising the step of receiving the first fluid flushed from the trunk channel in the reservoir.

32. The method of claim 31 wherein the reservoir comprises a microfluidic channel.

33. A device for metering a microfluidic plug of fluid from a larger fluidic volume, the device comprising:

a trunk channel having a fluidic inlet and a fluidic outlet; and a microfluidic branch channel in direct, independent fluid communication with the trunk channel, the branch channel having a fluidic impedance region;

wherein the trunk channel, branch channel, fluidic inlet, fluidic outlet, and fluidic impedance are arranged to permit a first fluid to be supplied through the trunk channel to fill the branch channel to the fluidic impedance region, and thereafter to permit the fluidic contents of the trunk channel to be flushed through the fluidic outlet while the branch channel remains substantially filled.

34. The device of claim 33, further comprising a plurality of sub-branch channels in fluid communication with the microfluidic branch channel.

35. The device of claim 33, further comprising a plurality of microfluidic branch channels, each in direct, independent fluid communication with the trunk channel.

36. The device of claim 33 wherein the microfluidic branch channel has a volume of less than about two microliters.

37. The device of claim 33 wherein the microfluidic branch channel has a volume of less than about one microliter.

38. The device of claim 33 wherein the microfluidic branch channel has a volume of less than about five hundred nanoliters.

39. The device of claim 33 wherein the fluidic impedance region comprises a passive valve.

40. The device of claim 33 wherein the fluidic impedance region comprises an active valve.

41. The device of claim 33 wherein the fluidic impedance region comprises an overlap region.

42. The device of claim 33 wherein the fluidic impedance region includes a porous membrane.

43. The device of claim 42 wherein the porous membrane includes a plurality of porous regions.

44. The device of claim 33 wherein the branch channel has an associated gas-permeable vent.

45. The device of claim 33 wherein the trunk channel is a microfluidic channel.

46. The device of claim 33, further comprising multiple microfluidic branch channels each in independent, direct fluid communication with the trunk channel.

47. The device of claim 33 wherein the device is fabricated with a plurality of device layers.

48. The device of claim 33 wherein any device layer of the plurality of device layers is a stencil layer.

49. The device of claim 33 wherein any device layer of the plurality of device layers is fabricated with a polymeric material.

50. The device of claim 33 wherein any device layer of the plurality of device layers is fabricated with a self-adhesive tape material.

* * * * *

UNITED STATES PATENT AND TRADEMARK OFFICE
CERTIFICATE OF CORRECTION

PATENT NO. : 6,481,453 B1
DATED : November 19, 2002
INVENTOR(S) : O'Connor, Stephen D. et al.

It is certified that error appears in the above-identified patent and that said Letters Patent is hereby corrected as shown below:

Column 1,
Lines 65 and 66, the phrase "4783-4789) However," should read -- 4783-4789); however, --

Column 3,
Line 43, the phrase "qualities that are incompatible particular conduit" should read -- qualities that are incompatible with particular conduit --

Column 8,
Line 5, the phrase "For example, the second fluid may a gas that" should read -- For example, the second fluid may be a gas that --
Line 8, the phrase "the extremely small fluid/gas interface are, is very slow" should read -- the extremely small fluid/gas interface is very slow --

Column 15,
Line 43, the phrase "The method of claims 1 wherein" should read -- The method of claim 1 wherein --

Column 16,
Line 37, the phrase "The method of claims 17 wherein" should read -- The method of claim 17 wherein --

Signed and Sealed this

Thirteenth Day of April, 2004

JON W. DUDAS
*Acting Director of the United States Patent and Trademark Office*